United States Patent [19]
Grandone et al.

[11] Patent Number: 5,282,149
[45] Date of Patent: Jan. 25, 1994

[54] ADAPTIVE SCHEDULING SYSTEM AND METHOD FOR A BIOLOGICAL ANALYZER WITH REPRODUCIBLE OPERATION TIME PERIODS

[75] Inventors: Cass J. Grandone, Lake Forest; Mark Pierce, Wauconda; Ilya Ratner, Highwood; Jeanine T. Douglas, Gurnee, all of Ill.

[73] Assignee: Abbott Laboratories, Abbott Park, Ill.

[21] Appl. No.: 709,721

[22] Filed: Jun. 3, 1991

[51] Int. Cl.$^5$ ............................................. G06F 15/46
[52] U.S. Cl. ..................................... 364/497; 422/67
[58] Field of Search ................. 364/497, 496; 73/863, 73/863.01, 863.11; 422/67; 436/34, 50, 47, 48

[56] References Cited

U.S. PATENT DOCUMENTS

| | | | |
|---|---|---|---|
| 4,796,197 | 1/1989 | Lissot et al. | 364/500 |
| 4,935,875 | 6/1990 | Shah et al. | 364/497 |
| 5,122,342 | 6/1992 | McCulloch et al. | 422/65 |
| 5,139,743 | 8/1992 | Ishizaka et al. | 422/63 |
| 5,154,889 | 10/1992 | Muraishi | 422/65 |
| 5,158,895 | 10/1992 | Ashihara et al. | 436/526 |
| 5,175,086 | 12/1992 | Takekawa et al. | 435/7.92 |

Primary Examiner—Jack B. Harvey
Assistant Examiner—Thomas Peeso
Attorney, Agent, or Firm—Richard D. Schmidt

[57] ABSTRACT

A biological sample analyzer, and a method and system for operation thereof, wherein instrument systems used to perform an assay of each of the biological samples loaded into the analyzer are operated in accordance with a schedule developed by a scheduler routine. The scheduler routine determines a time allowance for performing operations by instrument systems for conducting an assay on each biological sample from a load list indicating the type of assay to be conducted upon each biological sample. The time allowance determined is adapted to accommodate variations in actual performance of instrument system operations on each sample so that the assays of the biological samples can be performed by the instrument system operations in accordance with a reliable and reproducible schedule.

12 Claims, 4 Drawing Sheets

ADAPTIVE SCHEDULING SYSTEM AND METHOD FOR A BIOLOGICAL ANALYZER WITH REPRODUCIBLE OPERATION TIME PERIODS

REFERENCE TO RELATED APPLICATIONS

The disclosures of the following copending applications assigned to the assignee of the present application and filed concurrently herewith are specifically incorporated by reference:

"Adaptive Scheduling System and Method For Operating a Biological Sample Analyzer With Variable Interval Periods", by Kathy Burns, Ilya Ratner, Jeanine T. Douglas, Erica Kline, and Cass J. Grandone Ser. No. 07/709,723, filed Jun. 3, 1991;

"Adaptive Scheduling System and Method For Operating a Biological Sample Analyzer With Variable Rinsing", by Cass J. Grandone Ser. No. 07/709,195, filed Jun. 3, 1991;

"Retrofit Kit For Changing Single Immunoassay Instrument to Flexible Multiple Immunoassay Instrument", by Chadwick M. Dunn, Cass J. Grandone, Stephen L. Herchenback, Robert J. Nelson, Robert Perry, James T. Tyranski and Gary Lee Zuck Ser. No. 07/709,730, filed Jun. 3, 1991;

"Carousel For Assay Specimen Carrier", by Cass J. Grandone, Steven L. Herchback, Robert perry, James T. Tyranski and Gary Lee Zuck Ser. No. 07/709,726, filed Jun. 3, 1991.

"Heat and Air Flow Control For Assay Carrier", by Chadwick M. Dunn, Cass J. Grandone, James T. Tyranski and Kris T. Luddington Ser. No. 07/709,728, filed Jun. 3, 1991;

"Reagent Bottle and Cap", by James T. Tyranski Ser. No. 07/709,725, filed Jun. 3, 1991; and "Reagent Pack For Immunoassays", by Steven Herchenback, Robert Nelson, James T. Tyranski and Gary Lee Zuck Ser. No. 07/709,726, filed Jun. 3, 1991.

MICROFICHE APPENDIX

Included are two microfiche of 139 total frames.

BACKGROUND OF THE INVENTION

The present invention relates generally to biological sample analyzers used to perform assays of patient specimen samples. More particularly, the present invention relates to a method and system for the scheduling the operating steps for performing assays of biological samples in an automatic analyzer with reproducible and reliable performance.

Biological sample analyzers, of the type considered herein, are automated instruments that may be used in hospitals, clinics, laboratories, or other locations, to run routine tests (assays) on samples of patient specimens such as blood, spinal fluid, urine, serum, plasma, and so on. An automated analyzer of the type discussed herein includes an analyzer unit that runs tests on a number of patient specimen samples that are loaded into the unit. An operator-user prepares the samples by placing portions of the patients' specimen samples into a number of like-sized sample containers. These samples may be diluted or otherwise treated, depending upon the type of analyzer used, the type of assay being performed, and other factors. The containers are then placed in the analyzer unit. The containers may first be placed in a rack or carousel that is then placed in the analyzing unit. The rack may accommodate a number of sample containers, e.g. 24. In addition, one or more appropriate chemical reagents, needed to perform the assays, are also placed in the analyzer unit. In order to mix reagents with the samples, the analyzer unit may also include a fluid moving system, such as a robotic probe mounted on a boom, which is adapted to draw up portions of the reagents and/or samples and expel them into appropriate locations, e.g. additional cells such as reaction cells provided in the sample containers, where a reaction can take place. The analyzer unit also may include a means for detecting a reaction in the reaction cells. This may include an optical detector to observe fluorescence reactions and make optical measurements to obtain a result for each sample. The analyzer unit may also typically include other mechanical systems to move the sample containers and the probe. The analyzer unit may also provide for cleaning the probe between certain tasks in order to avoid contamination between samples. For this purpose, the analyzer unit may also include a washing station and a waste dispensing container to hold the used rinse solution.

After the operator-user loads the specimen samples, enters appropriate instructions, and starts the unit, the analyzer runs unattended. When placed in operation, the analyzer unit, using the appropriate chemical reagent, runs the same test on each of the samples in the sample containers and will perform identical operations on each of the samples loaded in the rack. When it is finished, the analyzer prints out or otherwise reports on the results of its testing.

Biological analyzers utilize different chemistries for performing assays of specimen samples. One type of assays used in biological analyzers includes immunoassays and solid phase procedures. Analyzers for performing immunoassays in general and enzyme immunoassays in particular are known in the art.

A biological analyzer that utilizes immunoassay chemistry to perform assays of specimen samples loaded therein is the IMx ® analyzer introduced in 1988 by Abbott Laboratories, of North Chicago, Ill. (A description of the IMx analyzer is included in "The Abbott IMx Automated Benchtop Immunochemistry Analyzer System", by Fiore, M. et al., *Clinical Chemistry*, Vol. 34, No. 9, 1988, which is specifically incorporated herein by reference in its entirety). The IMx analyzer is a biological sample analyzer that has been developed for use in conjunction with solid phase immunoassay procedures to perform a variety of assays (such as sandwich and competitive assays). The IMx analyzer uses a technology referred to as microparticle capture enzyme immunoassay (MEIA) and fluorescence polarization immunoassay (FPIA). The IMx analyzer includes a microprocessor used to control a robotic arm with 2 degrees of freedom and a rotating carousel to process the samples for assay. One assay can be done on each of 24 specimen samples in 30-40 minutes or more unattended after loading (i.e. with "walk away" automation). Assay results are output to a printer or a computer interface.

A biological sample analyzer, such as the IMx analyzer described above, can execute the steps required for performing assays of up to 24 specimen samples, including the steps of counting the samples, identifying which assay to run, warming the reagents and reaction cells to appropriate temperatures, pipetting the reagents and samples, diluting samples if required, timing critical assay steps such as incubations, washing unbound conjugate, quantifying the fluorescence signal and performing data reduction to yield a useful result.

The container used for holding each of the specimen samples for a biological sample analyzer, such as the IMx analyzer, may be a disposable assay cartridge having a plurality of wells, with at least one reaction well and one separation well. The separation well may contain a fibrous matrix positioned across its entrance and an absorbent material positioned below the fibrous matrix. Microparticles react with an analyte containing sample and one or more reagents to form a complex. This complex is immobilized on the matrix of the separation cell. The excess sample and reagent are washed through the matrix and captured in the absorbent material below.

The results of the reactions may be read using known optical detection techniques. For example, using conventional solid phase procedures, an analyte can be labeled or tagged with an enzyme which in the presence of its substrate fluoresces, and emits light at a known wave length. The rate at which the fluorescent product is produced is indicative of the concentration of the analyte in the biological sample. A conventional fluorometer is suitable for illuminating the fibrous matrix with a beam of light having the appropriate excitation wave length. The fluorometer also detects the intensity of the light at the emission wave length. Assays using this type of solid phase technology has been found to provide a high degree of sensitivity.

A biological sample analyzer, such as the IMx analyzer, provides for performing assays of patients' specimen samples and reading the results of such assays in a mass production type manner. This allows such assays to be made available quickly and conveniently.

Even though such analyzers can provide significant advantages by performing assays quickly and conveniently, further advantages for the user could be obtained if the overall through put of the analyzer could be increased. One way to provide even more advantages and convenience for users of biological analyzers would be to provide the capability to perform more than one assay on the specimen samples in an unattended run. Although a biological analyzer like the IMx analyzer can perform different types of assays and can perform assays on a number of specimen samples unattended, the analyzer can run only one type of assay at a time. If a different type of assay is to be performed, the analyzer would have to be reloaded with different reagents. Also, because different types of assays may require different amounts of the sample specimen, different amounts of reagents, different processing steps, different incubation times, etc., the analyzer would also be reset at the beginning of the run to perform the new assay. In the case of the IMx analyzer, a different memory module may have to be inserted containing instructions for the analyzer unit for performing the different assay. Thus, even if only a few of several different types of assays need to be run, the operator-user has to load and run the analyzer for the first type of assay for only a few samples and then reload the analyzer to run the second type of assay on another batch of samples using perhaps different reagents. It is recognized that for many users of the IMx analyzer, or other biological sample analyzers, it would be convenient and advantageous to be able to perform more than one type of assay during an unattended run.

Although it may be desirable to provide a biological analyzer with the capability to perform more than one assay in an unattended run, there are several obstacles that make providing this feature complicated. For example, different assays require different functions or operations to be performed upon the sample specimens in the carousel rack by the mechanical or optical systems of the analyzer. In the prior IMx analyzer, or in other analyzers in which only one type of assay is being performed during an unattended run, it can be difficult to determine when each of the operations upon each of the samples will be performed so that sufficient time allowance can be provided to ensure that incubation periods limits are not exceeded or that the samples or reagents do not evaporate. This is even more difficult in an analyzer in which the user is permitted to select the type and number of assays to be performed in an unattended run. For example, if there are 24 specimen samples in the carousel rack and the operator-user is permitted to select any one of three different assays to be performed on the samples, there are almost 2500 different permutations of possible combinations of assays and samples that the user can select. (The number is 2925 if all possible combinations, even those that an operator-user would never run are considered). If the user is permitted to select any one of four different assays to be performed on the 24 samples, there are approximately 10,000 different permutations of possible combinations. This presents an operating problem because certain tasks in the automatic analyzer must be performed on the samples at certain times or within certain specific time limits. Thus, there is a requirement to efficiently schedule the activities being performed by the automatic analyzer. Considering that 100 or more different mechanical operations can be performed on each sample, and that due to chemical reaction constraints certain operations must be performed within certain rigidly specified time durations from other operations in order to obtain valid results, it can readily be appreciated that scheduling and operating an analyzer to perform more than one assay unattended is considerably more complicated than scheduling and operating an analyzer in which only one assay is performed in an unattended run.

One automatic assay device is known having the capability to perform more than one assay on specimen samples loaded therein in an unattended (e.g. "walkaway") run. That device is the ADx ® biological analyzer available from Abbott Laboratories. Although the ADx analyzer can perform more than one type of assay on samples loaded in its carousel rack, the ADx analyzer is used primarily for assays that are different than those performed by the IMx analyzer. The assays performed by the ADx analyzer are, in general, simpler and typically include fewer steps. Also with respect to the assays performed by the ADx analyzer, there are, in general, fewer constraints on incubation periods between steps. Accordingly, when the ADx biological sample analyzer is used to perform more than one assay in a run, the scheduling of the various operations to be performed by the analyzer systems on the specimen samples can be accomplished by using the minimum incubation time interval between operations. However, when the minimum incubation period is used, the throughput of the analyzer can decrease (i.e., the overall time to run the assays increases) due to conflicts among the schedules of the assays. Moreover, with the type of assays performed by the IMx, such as MEIA and FPIA, there are usually more steps for each assay and there are more constraints that certain steps must be performed within certain incubation time limits to produce valid data. Further, with the types of assays performed on the IMx analyzer, there is also greater variability in the assay steps and incubation limits between different steps among different assays. Accordingly, it is difficult to schedule an analyzer such as the IMx analyzer to perform more than one assay in an unattended run.

One of the factors affecting the scheduling of instrument operations is the variation in time that it takes to perform certain operating steps by the analyzer on the specimen samples. Such variations in operation can arise in numerous ways. One of the ways that variations can arise relates to the number of possible schedule permutations as a result of scheduling more than one assay to be performed in a run.

With an analyzer capable of performing more than one assay in a run, the number of possible permutations of load lists is high thereby complicating the scheduling of the analyzer instrument system operations to account for such variations. It can be appreciated that the functions being performed by the analyzer instrument systems involve certain mechanical operations, such as moving a boom and probe, aspirating a reagent, sample, or rinse, moving the carousel rack, "step-look" operations to find a fluid level, etc. The amount of time that these operations take is a function of the start and stop positions of the probe, the rack, the reagents, etc., and can also vary depending upon the number and location of each type of sample being run for each type of test.

For example, the movement of the carousel can take different amounts of time depending upon whether the carousel has to move only a few degrees or whether it has to move a complete half revolution. Evidently, the half rotation takes longer to perform than the movement of only a few degrees. However, when attempting to schedule the operation of the analyzer instrument systems, these variations in position are a factor and can add up over a run. Since such variations in movement time are a function of both the previous and subsequent positions of the instrument system, these variations cannot be accounted for until both all these positions are established.

Also, there may be certain variations related to training calibration points, interrupt latencies, the clock speed of the microprocessor, code running overhead, motor controller variations, etc. In addition, there may be variations between different machines due to design tolerances among machines. Also, certain analyzers may have minor idiosyncracies that affect the time that it takes to perform certain instrument system operations but that do not detract from safe reliable performance.

Although it may be technically possible to calculate a prediction that closely approximates the amount of time variations in instrument activities should take based upon the start and stop location of the instrument systems, such an effort would be burdensome and require a significant amount of processing power. Moreover, such detailed calculation might not necessarily account for the design tolerances from one analyzer to the next mentioned above or certain idiosyncracies associated with certain analyzers.

These variations in performance times can complicate the operation of the analyzer because certain assay steps such as incubation periods, must be performed within specific defined time periods of other steps to provide valid data. Because these incubation periods must be strictly observed if the analyzer completes certain instrument operations too quickly or too slowly it can exceed the required time limits.

Thus, the scheduling of the operating steps of an analyzer becomes very burdensome and complicated especially when more than one assay is being performed in an unattended run.

Accordingly, it is an object of the present invention to provide a biological analyzer that is capable of performing more than one assay on specimen samples loaded therein in an unattended run in a manner that provides reasonable through put.

It is a further object to provide a biological analyzer that accounts for variations in instrument system movements and locations, machine tolerance variations and other factors and provides a reliable and reproducibly consistent assay performance.

SUMMARY OF THE INVENTION

The present invention provides for a biological sample analyzer, and a method and system for operation thereof, wherein instrument systems used to perform assays of the biological samples loaded into the analyzer are operated in accordance with a schedule developed by a scheduler routine. The scheduler routine determines a time allowance for performing operations by instrument systems for conducting an assay on each biological sample from a load list indicating the type of assay to be conducted upon each biological sample. The time allowance determined is adapted to accommodate variations in actual performance of instrument system operations on each sample so that the assays of the biological samples can be performed by the instrument system operations in accordance with a reliable and reproducible schedule.

It is an advantage of the present embodiment of the invention that the significance of sample position, reagent pack position, and instrument parameters (e.g. boom calibration, etc.) can be eliminated from consideration in scheduling. This can be done by providing a time allowance sufficient to account for a "worst-case" time for performance for each instrument system movement or command.

It is an advantage of operating an analyzer in this manner that the number of permutations of possible schedules is greatly reduced. Whereas, positional variations and machine-to-machine variations can generate an almost infinite number of permutations and be exceedingly difficult to account for, with the scheduling method of the present embodiment, the number of possible permutations is limited to the number of load list combination permutations. Assuming a maximum of three types of assays per run this number is only 2925. Of course, in analyzers with a different number of samples or with a different number of possible assay types, the number would be different.

It is yet another advantage of the present invention that a biological analyzer incorporating the present invention should be able to obtain regulatory validation more readily because the operation thereof can be proven with a great deal of certainty for a large number of instruments.

For purposes of this specification and claims, a "run" is considered to refer to the operation of the analyzer in performing the assays after the operator-user has loaded into the analyzer the specimen samples, reagents, rinse, or other accessory material and also entered any necessary information pertaining to the assays to be performed on the samples. The "run" concludes when the assays have been performed on all the samples and may include data analysis performed in generating an assay test result or printing or otherwise outputting the results of the assays. In automatic analyzers of the type considered herein, the run may proceed unattended.

DETAILED DESCRIPTION OF THE PRESENTLY PREFERRED EMBODIMENTS

Figure 1:
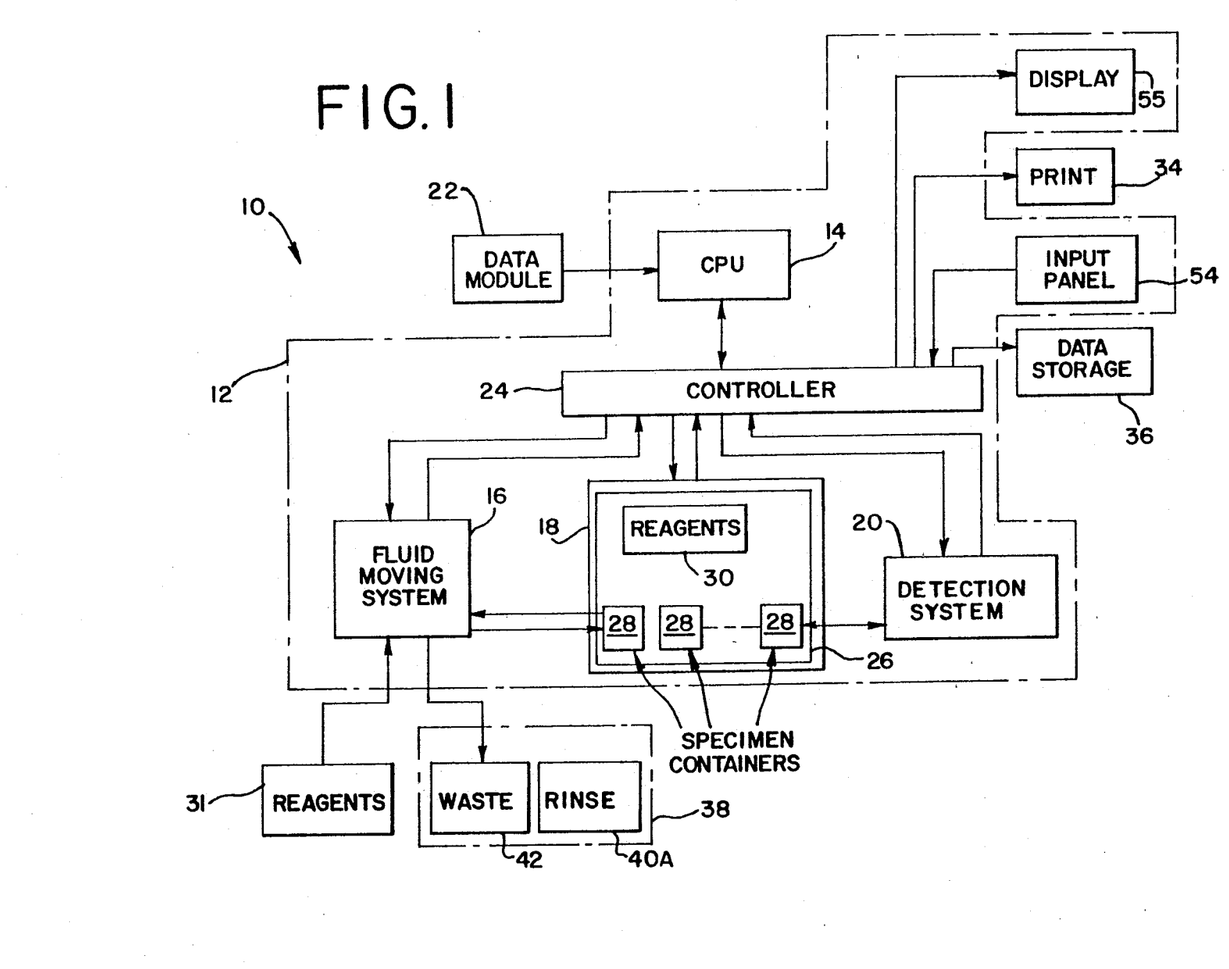
FIG. 1 is schematic of a biological sample analyzer incorporating aspects of a first presently preferred embodiment of the present invention.

Referring to FIG. 1, there is depicted a schematic block diagram of a biological sample analyzer 10 of a first embodiment of the present invention. The biological system analyzer 10 includes an analyzer unit 12, in which is included a CPU 14. The CPU 14 operates analyzer unit instrument systems in accordance with means well known to those skilled in the art. The analyzer unit instrument systems include a fluid moving system 16, a carousel moving system 18, and a detection system 20. Additional systems may also be included. One or more modules 22 include programming, stored for example in a PROM, used for the operation of the analyzer unit 12 and the analyzer unit systems. The programming on these modules 22 may include separate programs specifically adapted for performing specific different types of assays. These modules 22 may be removable to provide for additional different assays to be performed as well as to readily provide for updates and improvements to the system operation to be implemented. The analyzer unit instrument systems 16, 18 and 20 operate through an appropriate controller-interface 24. In this embodiment, the CPU 14 used is an Intel Model 80286 microprocessor.

The carousel moving system 18 is adapted to move a carousel or rack 26 upon which is positioned a plurality of patient specimen sample containers 28. The carousel 26 is preferably removable in order to facilitate loading and unloading of the patient specimen sample containers 28 into the analyzer unit 12. The carousel 26 may also hold a first set of one or more reagents 30 for performing a particular assay. A second set of one or more reagents 31 may also be included in the analyzer unit 12 in a location off of the carousel 26. These reagents may be in reagent packs and may include reagents for performing MEIA and/or FPIA types of assay tests, as described above.

The fluid moving system 16 includes one or more robotic pipette-booms adapted to move fluid from one location to another in the analyzer unit 12, e.g. from one container to another, under the control of the CPU 14.

The CPU 14 operates the carousel moving system 18 to move the carousel 26 and the fluid moving system 16 to move the pipette-boom to mix the appropriate reagents with the specimen samples in the containers 28. The CPU 14 also operates the carousel moving system 18 to move the carousel 26 and thereby the containers 28 into position to observe reactions at the detection system 20. The CPU 14 controls the detection system 20 which may include means for detecting florescence reactions in a manner that is well known in the art. In a preferred embodiment, the detection system 20 includes a low pressure mercury lamp used in a fluorometer. The CPU 14 receives the information about the reactions from the detection system 20 and performs the appropriate data analysis, and outputs results to either a printer 34 or to a data storage 36. A cleaning station 38 may also be provided in the analyzer unit 12. The cleaning station 38 includes a rinsing solution 40A and a waste container 42 into which waste fluid can be dispelled.

Figure 2:
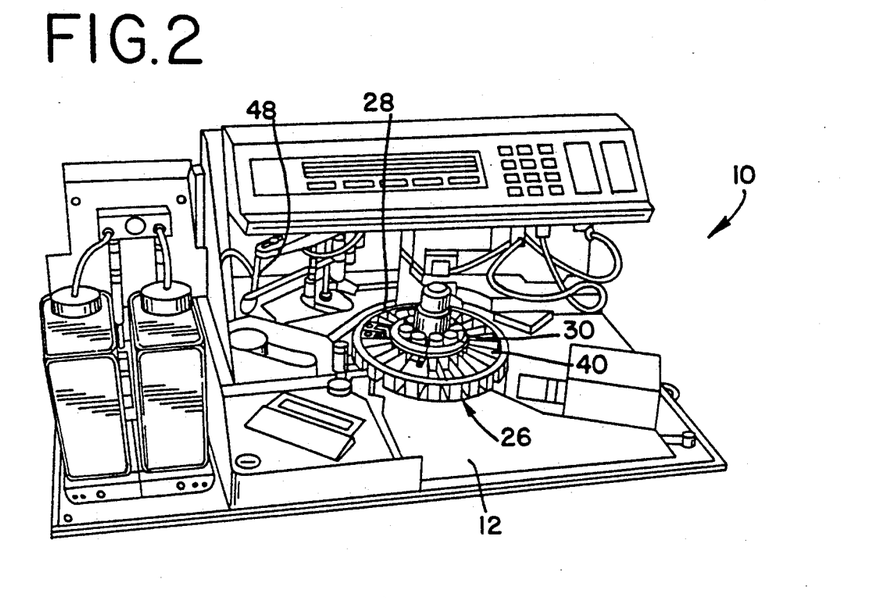
FIG. 2 is a perspective view of a biological sample analyzer (with a cover portion removed to reveal components therein) of the embodiment of FIG. 1.

FIG. 2 depicts a perspective view of the biological sample analyzer 10 incorporating aspects of the first embodiment of the present invention. The analyzer unit 12 holds the circular carousel rack 26 into which are placed a plurality of assay container cartridges 28. These cartridges 28 are preferably disposal. The assay container cartridges 28 are placed in a plurality of openings 40 (also referred to as "wedges") arranged around a central core of the carousel rack 26 which is specially formed to hold the cartridges. All the cartridge containers 28 have individual alignment features that insure their accurate alignment within the rack 26.

The carousel rack 26 containing the cartridge containers 28 can be circularly indexed to accurately position each assay cartridge container relative to the detection system 20 containing a optical reading apparatus. Because the reading positioning is highly accurate, the assay is properly positioned for reading at a reading station.

The fluid moving system 16 includes a pipette/probe assembly that include syringes 48 (e.g. a 250 microlater sample syringe and a 2500 microlater diluent syringe may be provided) driven by stepper motors. The pipette/probe assembly can be positioned over the reagents 30, the individual cells of the containers 28, or the wash station 38. Stepper motors move the pipette system up and down as well as radially. The fluid moving system 16 transfers fluid from reagent bottles to separation wells and from well to well. The pipette itself is a drawn stainless steel tube, teflon coated to minimize carryover. Fluid levels may be sensed by measuring electrical conductivity between the pipette pro tip and an externally electrode.

Carryover between samples and reagents is minimized by washing the pipette/probe over a wash station.

Because enzyme immunoassays require precise temperature control to achieve repeatable performance, heating elements (not shown) are provided in the analyzer unit 12.

The biological analyzer 10 illustrated in FIG. 2 is similar to the prior analyzer (the IMx analyzer) sold by Abbott Laboratories, Inc. Compared to the prior analyzer, this embodiment of the analyzer includes additional reagents 30 that are stored in the carousel 26 in the analyzer and are used to perform the greater-than-one assays during a run. This embodiment of the analyzer also includes additional programming to perform the greater-than-one assays during a run.

Figure 3:
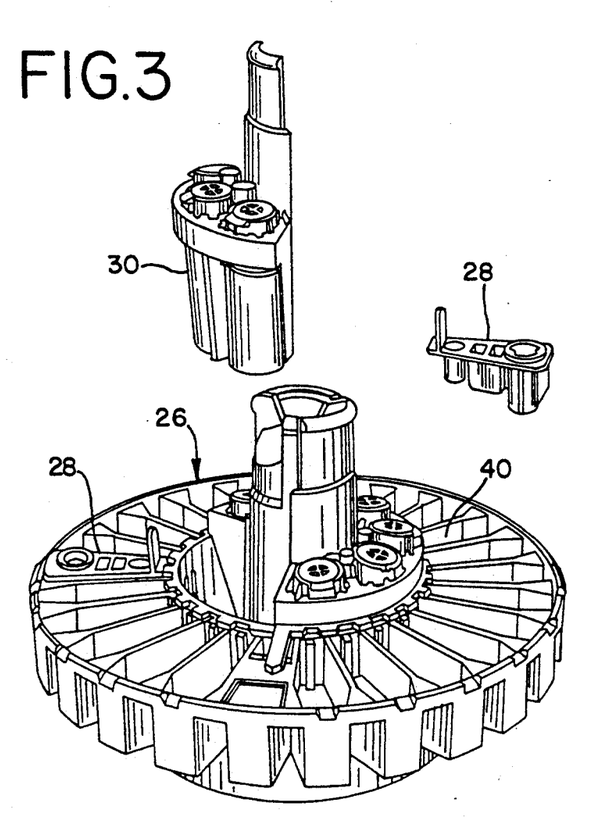
FIG. 3 is a perspective view of the carousel rack of the embodiment shown in FIG. 2.

As shown in FIG. 3, a first set of reagents 30 are included on the carousel 26. In a preferred embodiment, these reagents 30 are included on a portion of the carousel 26 and located centrally of the sample wedges 40.

An operator-user prepares for an assay run sequence by loading containers containing patient specimen samples (sometimes referred to as "disposables") into the carousel 26. In this embodiment, approximately 150 microliters of sample, controls, or calibrators is added to a sample well of each of the reaction cells of the container. The carousel rack is then placed in the analyzer unit 12 and the appropriate reagent pack or packs are loaded into the unit or the carousel.

In this embodiment of the analyzer 10, the operator-user also includes a calibration sample for each assay type being run. Thus, if three different types of assays are being run, three separate calibration samples are also run. The calibration samples have a known amount of the substance being tested for, and accordingly, are used as a basis for determining the amounts of the tested for substance in the unknown specimen samples by comparison of the reactions. This use of calibration samples is similar to what has been performed in the prior IMx analyzer. Typically, the calibration samples occupy specific positions (i.e. wedges) in the carousel rack 26.

The operator-user enters a load list. This may be done by means of the input panel 54 (of FIG. 1). The entry of the load list may be prompted by a menu on the display 55. The load list identifies the wedges of the carousel in which patient specimen samples are located and which assay is to be run on each of the specimen samples. Not all of the wedges of the carousel have to be used. The operator-user has the option of selecting several different assays to be performed automatically in a single run and also has the option of selecting the number of specimen samples to be used for each different assay. In a preferred embodiment up to four different assays may be available, however, the present invention could be extended to even a greater number. In a preferred embodiment, the samples upon which the same assay is to be performed are grouped together, i.e. in adjacent wedges of the carousel. This facilitates input of the load list by allowing the operator-user to indicate at which wedge position the specimen samples for a specific assay begin.

For purposes of efficiency, certain types of assays will be typically grouped together. For example, the assays for Prolactin, LH and FSH will be typically grouped together and the tests for CEA, AFP, and CA 19-9 will be grouped together. Other grouping of assays can be provided. These groupings are based, in part, upon the likelihood that an operator-user would want to run these assays at the same time. These combinations could be changed to include other assays or delete assays if different combinations would be preferred. If a different combination of assays were included, the appropriate reagents for those assays would be loaded in the analyzer unit.

Although in a preferred embodiment, the user-operator enters a load list by inputting information into the input panel 54, the load list for a run may be entered by other means. For example, the load list could be entered via a computer or communications interface. Alternatively, the load list may be determined automatically by scanning information attached or otherwise associated with each specimen sample container.

After closing a door or otherwise performing any other steps for preparing the analyzer unit, the operator-user actuates a run button on the input panel 54 of the analyzer unit. From this point, the analyzer can operate automatically and unattended until all the assays are finished.

Under the control of a program run on the CPU 14, the analyzer unit 12 begins a preparation process in which the following actions typically are taken: all stepper motors (fluids, syringe pumps, carousel motor, pipette system motors) are "home" (adjusted to times 0), the carousel rack is scanned to identify the type of carousel installed and its "lock" status. The reagent pack types may be read by a bar code scanner located on the pipette system to identify or confirm the assays to be run. The carousel heating systems warm the reagents and reaction cells to the appropriate temperatures by directing heated air throughout the carousel as described in the copending application referred to above. The program also calls a scheduling program that schedules the operations to be performed by the instrument systems on the specimen samples.

Figure 4:
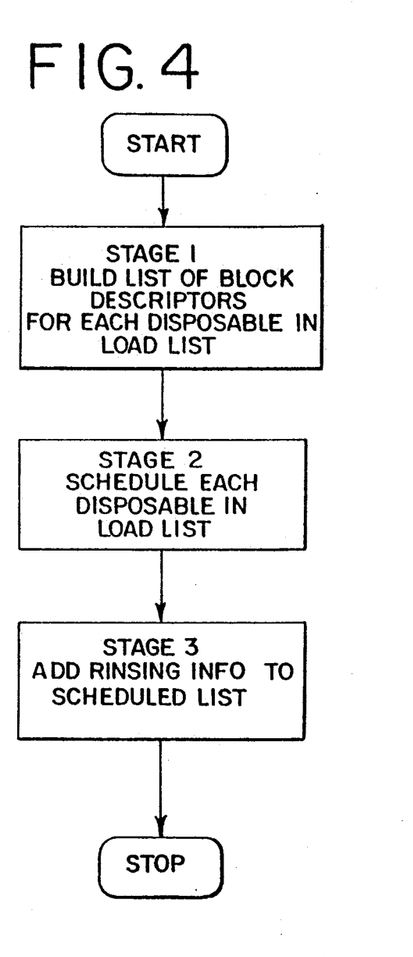
FIG. 4 is a block diagram flow chart depicting operating stages of a scheduler routine for operating the embodiment of the invention shown in FIG. 1.

FIG. 4 is a flow chart illustrating the program operation for the scheduler program 60 used to schedule the operations to be performed by the analyzer unit to perform the assays on the load list in accordance with one embodiment of the present invention. The scheduler program allows for scheduling the tasks performed by the analyzer in order to assure that certain tasks are performed within allowable time frames and with favorable through put. STAGE 1 includes procedures for creating a list of time blocks, a block descriptor for each time block, estimating the running time for each block, and sorting the load list. STAGE 2 includes procedures that establish the schedule of time blocks for each specimen sample so that the operations of a time block of a sample being scheduled do not conflict with any time blocks of any samples that have already been scheduled and that incubation limits between time blocks are not exceeded. STAGE 3 includes procedures for inserting rinsing information between or before time blocks.

Figure 5:
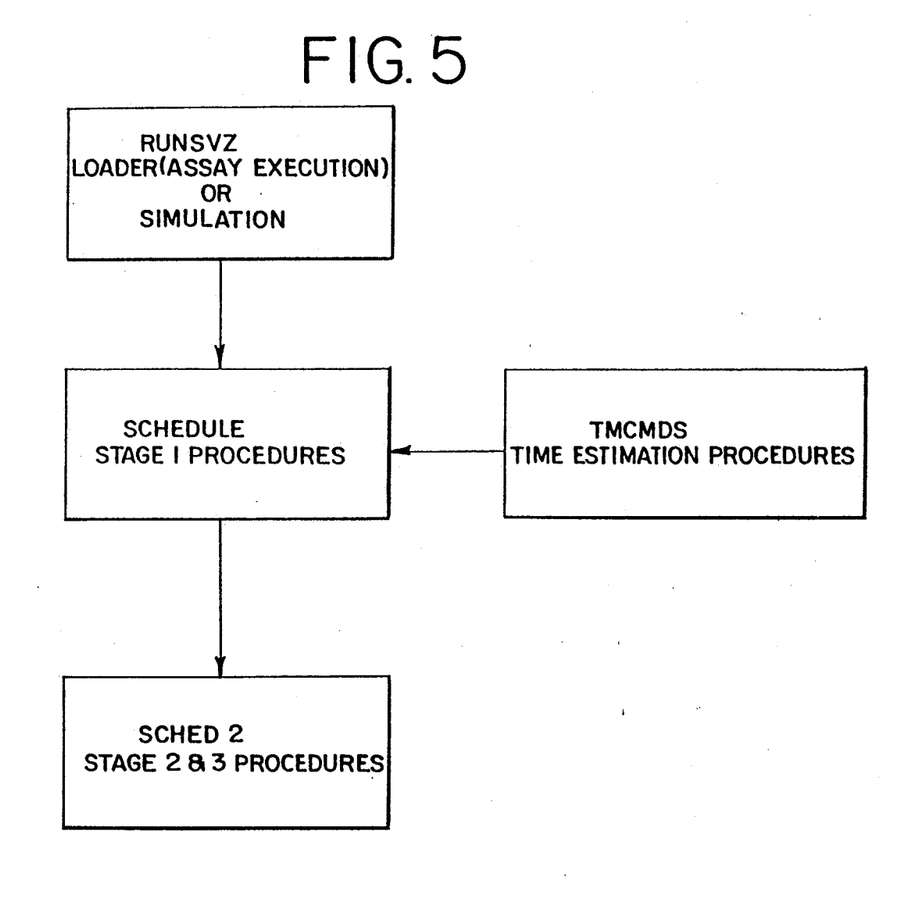
FIG. 5 is a block diagram flow chart depicting a portion of the program routines included on the module for operation of the embodiment of FIG. 1.

Referring to FIG. 5, there is a flow chart illustrating the program routines for operating the analyzer and calling the scheduler routines. A first routine RUNSVZ begins the operation and performs certain initialization procedures. RUNSVZ calls the SCHEDULE program that includes the STAGE 1 procedures. Time estimations for performing "blocks" of commands are developed in the TMCMDS routine and output to the SCHEDULE file. SCHEDULE calls SCHED2 that includes STAGE 2 and STAGE 3 procedures. TMCMDS.LST, SCHEDULE.LST, and SCHED2.LST are included in Appendix 1 of this specification.

Figure 6:
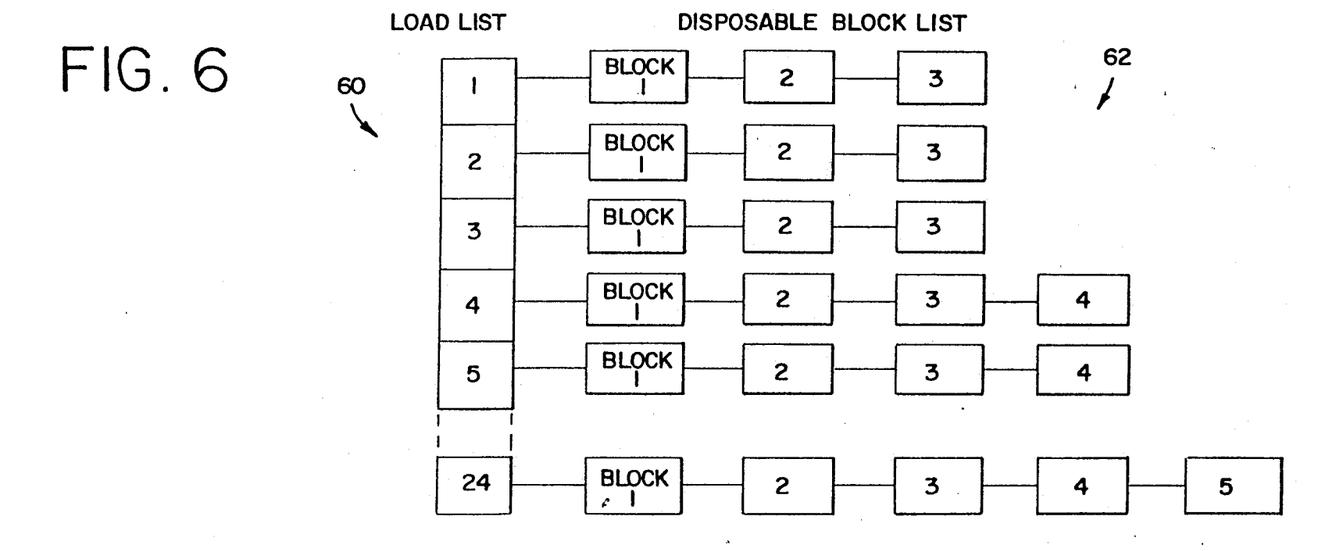
FIG. 6 is a diagram showing correspondence between a load list and lists of block descriptors associated with each specimen sample as developed by the STAGE 1 procedures of FIG. 4.

Referring to FIG. 6, there is a diagram showing correspondence between the load list 60 and lists of block descriptors 62 associated with each specimen sample as developed by the STAGE 1 procedures of FIG. 4. Based upon the entered load list, the STAGE 1 procedures develop time allowances for the operations to the performed by the analyzer unit instrument systems upon each specimen sample. The load list 60 indicates the sample specimen, e.g. Samples 1-24. The time allowances are organized into "time blocks", 1, 2, 3, associated with each of the samples. The time blocks represent one or more operations or activities to be performed by the analyzer systems upon or for that sample. Each specimen sample typically has associated with it several time blocks. For example, Sample I (as well as Samples 2 and 3) has three time blocks associated with it, Sample 4 has four time blocks associated with it, and Sample 24 has five time blocks associated with it. According to this embodiment of the invention, the time blocks establish when an analyzer unit resource (e.g. an instrument system) is occupied with a task associated with a sample. Accordingly, only one time block can take place (i.e. be performed) at a time.

Each of the time blocks of each specimen sample has "block descriptors" associated with it. The block descriptors contain such information such as which sample the block is associated with, how much time will be allowed to perform the steps in this time block.

After the STAGE 1 procedures are completed, the scheduler program calls the STAGE 2 scheduler procedures. The STAGE 2 procedures actually develop the schedule of time blocks generated by STAGE 1. The sample having the highest assigned priority sequence number is scheduled first. As mentioned above, the sequence number does not necessarily correspond to which assays are started first, but rather to which samples are scheduled first. It is evident however that the assay for the sample with the highest priority will begin first because it will be scheduled first and there will be no constraints on scheduling the time blocks of that sample. It is also likely that other assays for samples with high priorities will also tend to be begun sooner.

Referring again to FIG. 4, after the STAGE 2 procedures are completed, including the determination of the minimum intervals between time blocks and the scheduling of the time blocks, STAGE 3 procedures are performed. STAGE 3 procedures include the scheduling of necessary and appropriate rinse operations between time blocks.

Figure 7:
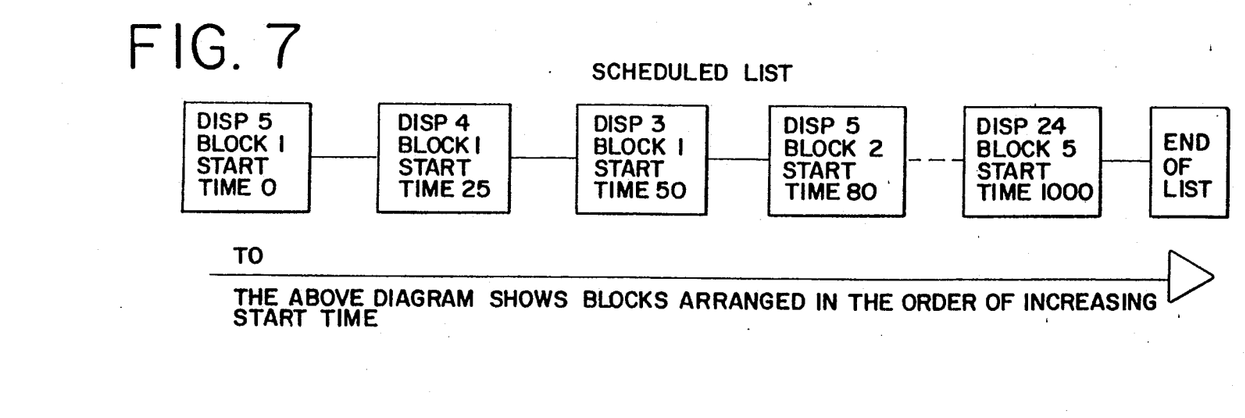
FIG. 7 is diagram depicting an example of a portion of the schedule blocks for all specimen samples to be scheduled and performed by the analyzer of FIG. 1.

Referring to FIG. 7, there is depicted a diagram illustrating an example of a portion of the sequence of time blocks scheduled by the scheduler program, above. Note that a start time has been assigned to each time block. The analyzer can then use the schedule to perform the assays of the specimen samples.

After the schedule is complete the analyzer unit can run the assays following the developed schedule. At the end of the instrument system operations and output of the data, the assays are completed.

Accordingly, in this aspect of the invention, the time estimation portion of the scheduling routine (STAGE 1) uses a system based upon a so-called "worst case" estimate. As mentioned above, a "time block", which is fixed, is allowed for each instrument system activity. This fixed time is determined to be the maximum time that a properly functioning analyzer would take to perform the instrument operation. This would assume, for example, that mechanical systems have to make the largest allowed movement. If the actual operation is completed before expiration of this fixed block of time, a variable length dead time of no activity is commanded to maintain the preset schedule developed in STAGE 2.

For example, if the mechanical task is to rotate the rack and move the probe, the block of time given to this task is based on the assumption that the rack must make a maximum rotation and that the probe must also make its maximum movement. Unless a "worst case" maximum time were enforced, certain tasks could be performed ahead of time or the tasks could be performed out of order. By establishing a maximum time, scheduling becomes considerably simplified and a significant reduction of overall time is obtainable.

The principle of operation of this embodiment is demonstrated by reference to the protocol example included in Appendix 2 to this specification. A protocol is a program routine prepared by an assay developer to provide instructions to the analyzer to perform the necessary operating steps for performing the assays on the specimen samples loaded into the analyzer. The protocol is stored on the module 22 and called by the analyzer operating routine to perform the assays. The protocol is written in CLI (command line interpreter) which is a high level programming language specifically designed for assay developers for operating the analyzer. By using a high level programming language specifically tailored to operate the analyzer, the assay developer is relieved of the burden of learning to program the detailed analyzer instrument system operations. Instead, the CLI language permits the assay developer to concentrate on the chemistry of the assay.

In the protocol example shown in Appendix 2, the command "RI" in line 2 instructs the analyzer to perform a rinse operation. "MB dilu" means to move the boom to the diluent. "AS" means to aspirate.

According to this embodiment of the invention, blocks are designated in the assay protocol. The block begins with the command "B 0" and ends with the command "E". Protocol commands that instruct the analyzer to perform operations that may take a variable amount of time to perform are included between in the block between the "B 0" and "E" commands. Other commands may be placed between the "B 0" and "E" commands as well. A time allowance is determined for each time block during the STAGE 1 time estimation procedures. The time allowance is determined based upon a "worst-case" estimate of the relative instrument system locations, instrument system speed, machine-to-machine variations, processor clock speed, and other factors that may affect how long the analyzer might take to perform the operating steps ordered by the commands in the time block of the protocol.

For example, when a protocol command calls for aspirating a fluid from a bottle with a pipette, a time allowance for this step is determined assuming that the bottle is empty or nearly so and that the pipette has to "step-and-look" all the way to the bottom of the bottle to reach the fluid. In carrying out this operation, the pipette will probably not have to step-and-look all the way to the bottom, however, for purposes of determining a time allowance for the block, the container is assumed to be empty. Thus, the time allowance will always provide sufficient time to perform the steps in the time block.

In another example, the carousel is assumed to require 1800 steps to make one revolution. Therefore, in determining a time allowance for carousel movements, 900 steps (half a revolution) is assumed to be required. Thus, the time allowance will always be sufficient to account for the execution of the command regardless of the variations that may arise. A safety factor time is also provided to ensure that the time allowance is sufficient to account for all variations. Then, the scheduler portion of the program in STAGE 2, schedules the analyzer instrument system operations by scheduling the time blocks. Since the variations described above have been accounted for by the "worst-case" estimation and safety factor into the time allowance for each time block, the schedule developed by the scheduler program for performing the time blocks for any permutation of the load list is consistent and reproducible.

According to the present embodiment, the scheduling of analyzer system operations can be made as a function only of the load list. Although the number of possible load lists is still high, e.g. more than 2500 possible combinations for three assays and 24 samples, this number is manageable. Further, by making scheduling of analyzer system operations a function of the load list only, the influence of sample position, reagent pack position, and instrument parameters can be eliminated from consideration in scheduling (by providing a time allowance sufficient to account for a "worst-case" time for each movement), the number of permutations of possible schedules is grossly reduced.

A significant advantage of the present embodiment is that the schedule of time blocks can be made always reproducible. Thus, scheduling difficulties due to machine to machine operating variations can be eliminated. Also, with this embodiment the schedule developed can guarantee that instrument system operations observe specific specified incubation time limits. In addition, with this embodiment, troubleshooting of the analyzer can be facilitated because, for any load list permutation, it can be determined the exact order and sequence of instrument system operations down to the time block and further it can be determined at what time each set of operations associated with each time block should commence.

In other embodiments, it would be possible to take into consideration some of the operating factors mentioned above. For example, it may be possible in further embodiments to account for the locational variations, such as whether the carousel moved 3° or 180°. Although it would be possible to calculate such variations and it may be possible to further improve the through put of a biological sample analyzer by using a closer estimate for certain movements based upon the starting and ending location, even in these further embodiments, it would be preferable to use the method described above to eliminate machine-to-machine variability to ensure proper operating conditions for performing the assays regardless of such variations.

Although the present invention has been described in terms of a biological analyzer that operates automatically and unattended (e.g. in a "walk-away" mode in which the operator-user does not add or remove specimen during a run), it is understood that the present invention can readily be adapted to an "interruptable" mode analyzer in which the processing of the samples during a run can be interrupted so that an additional sample may be added. In such an analyzer, the processing program would modify the interrupted schedule so that the desired assay could be performed on the added specimen sample in a similar manner as if it were part of the original load list.

In a further embodiment of the present invention, a "paneling" feature could be provided. With "paneling", separate patient samples would not have to be prepared when it is desired to run several different assays on the same patient's sample. To provide this feature, one or more disposable cartridges not containing any patient specimen sample could be loaded into the carousel rack in addition to the cartridge containers having patient specimen sample. The fluid moving system of the analyzer would then move portions of the patient's specimen sample from the one disposable in which it had been provided, and pipette it to the disposables not containing the patient's sample. Thus, the analyzer unit can relieve the operator or others from the need for preparing separate containers.

It is intended that the foregoing detailed description be regarded as illustrated rather than limiting and that it is understood that the following claims including all equivalents are intended to define the scope of the invention.

| APPENDIX 2 PROTOCOL EXAMPLE |
|---|
| *** BLOCK 1 *** |
| 1 B O |
| 2 RI 2100 500 700 8 |
| 3 MB dilu |
| 4 AS 145 175 400 3 |
| 5 MB uper |
| 6 AS 40 0 400 3 |
| 7 MB spcm |
| 8 AS 15 0 400 3 |
| 9 MB rwc1 |
| 10 DS 190 10 400 5 12 |
| 11 MB prew |
| 12 DS 10 165 400 7 7 |
| 13 MI 300 2100 |
| 14 E |
| *** BLOCK 2 *** |
| 15 B O |
| 16 RI 2100 500 700 8 |
| 17 |
| 18 MB rwc2 |
| 19 AS 150 200 400 3 |
| 20 MB tab |
| 21 DS 150 0 400 6 10 |
| 22 S 2 |
| 23 X |
| 24 DS 0 200 150 6 12 |
| 25 MI 0 2700 |
| 26 E |
| *** BLOCK 3 *** |
| 27 B O |
| 28 RI 2100 600 700 8 |
| 29 |
| 30 |
| 31 |
| 32 MB conj |
| 33 AS 30 0 400 0 |
| 34 AS 50 25 400 3 |
| 35 MB tab |
| 36 DS 50 0 400 7 16 |
| 37 MB prew |
| 38 DS 30 25 500 4 4 |
| 39 MI 300 300 |
| 40 E |
| *** BLOCK 4 *** |
| 41 B O |
| 42 RI 2100 500 700 8 |
| 43 |
| 44 MB tab |
| 45 AS 0 200 400 0 |
| 46 DS 0 50 150 6 5 |
| 47 S 1 |
| 48 X |
| 49 DS 0 50 150 6 5 |
| 50 S 1 |
| 51 X |
| 52 DS 0 100 200 6 4 |
| 53 MI 300 1500 |
| 54 E |
| 55 |
| 56 |
| 57 |
| 58 |
| 59 |
| *** BLOCK 5 *** |
| 60 B O |
| 61 RI 2100 500 700 8 |
| 62 MB mup |

-continued

APPENDIX 2
PROTOCOL EXAMPLE

```
63 AS 30 25 400 0
64 AS 70 0 400 3
65 MB tab
66 DS 70 0 400 7 15
67 S 2
68 MC 0 read 1
69 X
70 RE 0 eia 500 700 8
71 MB prew
72 DS 30 25 500 7 7
73 E
74 Z
```

We claim:

1. An improved analyzer into which biological samples are loaded and having instrument systems to perform an assay of each of the samples loaded therein, the improvement comprising:
   means for determining a time allowance for performing operations by the instrument systems on each biological sample for the assay to be conducted, said time allowance of a sufficient duration to accommodate variations in actual performance of the instrument system operations on each sample;
   means for scheduling the instrument system operations for each sample in accordance with the time allowances determined; and
   means for conducting the assays of the biological samples by performing the instrument system operations in accordance with a schedule established by said scheduling means.

2. The improved analyzer of claim 1 in which the means for determining a time allowance further comprises:
   means for developing a list of time blocks for each sample from an entered load list indicating a type of assay to be performed on each sample, each of said time blocks having a time allowance for performing instrument system operations assigned to said time block; and
   means for scheduling the time blocks to perform the instrument operations on a specimen sample including means for determining a start time for each time block.

3. The improved analyzer of claim 2 in which the means for conducting the assays further comprises:
   means for beginning performing the instrument system operations assigned to a time block at the start time determined for said time block;
   means for continuing performing the instrument system operations assigned to the time block until the instrument systems operations assigned to said time block are completed; and
   means for waiting until a scheduled start of a next scheduled time block to perform instrument system operations assigned to said next scheduled time block.

4. The improved analyzer of claim 3 in which the means for conducting the assays further comprises:
   means for idling the analyzer instrument systems from completion of the operations assigned to the time block until a beginning of the next scheduled time block.

5. The improved analyzer of claim 2 in which the means for determining a time allowance further comprises:
   means for determining a time allowance based upon a maximum time duration for performing the instrument system operations in said time block.

6. An automatic immunoassay analyzer into which specimen samples can be loaded and having analyzer instrument systems for performing an assay of each of the samples comprising:
   (a) means for determining time blocks for each specimen sample, each time block having a time duration of a sufficient duration for accommodating the instrument system operations on a specimen sample determined by a protocol for the assay to be performed on the specimen sample;
   (b) means for scheduling the time blocks for each specimen sample; and
   (c) means for conducting the assays of the specimen samples by performing the operations of the scheduled time blocks.

7. A method for operating a biological sample analyzer having analyzer instrument systems to perform an assay of each sample loaded therein, the improvement comprising the steps of:
   determining a time allowance for performing operations by the instrument systems on each biological sample for the type of assay to be conducted, said time allowance of a sufficient duration to accommodate variations in actual performance of the instrument system operations on each sample;
   developing a schedule for operating the instrument systems for each sample in accordance with the time allowances determined; and
   conducting the assays of the biological samples by performing the instrument system operations in accordance with the schedule.

8. The method of claim 7 in which the step of determining a time allowance further comprises the step of:
   developing a list of time blocks for each sample from an entered load list indicating a type of assay to be performed upon each of the biological samples, each of said time blocks having a time allowance for performing instrument system steps assigned to said time block; and further in which the step of developing a schedule further comprises:
   developing a schedule for the time blocks to perform the instrument operations on a specimen sample including determining a start time for each time block.

9. The method of claim 8 in which the step of conducting the assays further comprises the steps of:
   beginning performing the instrument system operations assigned to a time block at the start time determined for said time block;
   continuing performing the instrument system operations assigned to the time block until the instrument systems operations assigned to said time block are completed; and
   waiting until a scheduled start of the next scheduled time block to perform instrument system operations assigned to said next scheduled time block.

10. The method of claim 9 in which the step of conducting the assays further comprises the step of:
    idling the analyzer instrument systems from a completion of the operations assigned to the time block until a beginning of the subsequent scheduled time block.

11. The method of claim 8 in which the steps of determining a time allowance further comprises the step of:

determining a time allowance based upon a maximum time duration for performing the instrument system operations in said time block.

12. A method for operating an automatic immunoassay analyzer having analyzer instrument systems to perform an assay of each biological sample loaded therein and in which more than one assay can be performed on biological samples loaded into the analyzer, and further in which analyzer instrument system operating steps performed on the biological samples to perform the assays are included in programmed instructions included in protocols, comprising the steps of:

(a) determining time blocks for each biological sample, each time block having a time duration of a sufficient duration for accommodating the instrument system operations on a biological sample determined by a protocol for the assay to be performed on the biological sample;

(b) scheduling the time blocks for each biological sample; and (c) conducting the assays of the biological samples by performing the operations of the scheduled time blocks.

* * * * *